United States Patent
Strack et al.

(10) Patent No.: US 6,369,292 B1
(45) Date of Patent: *Apr. 9, 2002

(54) ABSORBENT ARTICLES HAVING REDUCED OUTER COVER DAMPNESS

(75) Inventors: David Craige Strack, Canton; Ann Louise McCormack, Cumming; Timothy Ray Martin, Alpharetta, all of GA (US)

(73) Assignee: Kimberly-Clark Worldwide, Inc., Neenah, WI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/994,530

(22) Filed: Dec. 19, 1997

(51) Int. Cl.[7] .......................... A61F 13/15; A61F 13/20
(52) U.S. Cl. ....................... 604/370; 604/372; 604/378; 604/385.01
(58) Field of Search ................. 604/367, 370, 604/372, 374–379, 385.1, 385.01

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,855,046 A | 12/1974 | Hansen et al. |
| 3,938,522 A | 2/1976 | Repke |
| 3,981,306 A | 9/1976 | Krusko |

(List continued on next page.)

FOREIGN PATENT DOCUMENTS

| | | |
|---|---|---|
| EP | 0 471 114 | 2/1992 |
| EP | 0 526 225 | 2/1993 |
| EP | 0546837 | 6/1993 |
| EP | 0 602 613 | 6/1994 |
| EP | 0 627 177 | 12/1994 |

(List continued on next page.)

OTHER PUBLICATIONS

NRL Report 4364, "Manufacture of Super–Fine Organic Fibers" by V.A. Wendt et al.

NRL Report 5265 "An Improved Apparatus for the Formation of Super–Fine Thermoplastic Fibers" by K.D. Lawrence et al.

*Primary Examiner*—John G. Weiss
*Assistant Examiner*—K. M. Reichle
(74) *Attorney, Agent, or Firm*—Douglas H. Tulley, Jr.

(57) ABSTRACT

Absorbent articles having reduced outer cover dampness are provided and include a hydrophobic barrier layer positioned between an absorbent core and a breathable liquid impervious outer cover. The hydrophobic barrier layer, such as one or more layers of nonwoven webs, has a thickness of at least 0.03 cm and a hydrohead value of at least 18 millibars. The hydrophobic barrier layer does not significantly reduce the water-vapor transmission rate (WVTR) of the absorbent article when the absorbent core is dry yet significantly reduces the overall WVTR of the absorbent article once the absorbent core is wet. Thus, an absorbent article is provided having a WVTR that exceeds about 1500 grams/square meter 24 hours when dry and yet is less than 15,000 grams/square meter 24 hours when wet.

28 Claims, 3 Drawing Sheets

U.S. PATENT DOCUMENTS

| | | | |
|---|---|---|---|
| 4,041,203 A | 8/1977 | Brock et al. | |
| 4,093,765 A | 6/1978 | Schmidt | 428/134 |
| 4,100,324 A | 7/1978 | Anderson et al. | |
| 4,147,580 A | 4/1979 | Buell | 156/291 |
| 4,196,245 A | 4/1980 | Kitson et al. | |
| 4,282,874 A | 8/1981 | Mesek | |
| 4,306,559 A | 12/1981 | Nishizawa et al. | |
| 4,340,563 A | 7/1982 | Appel et al. | |
| 4,341,216 A | 7/1982 | Obenour | |
| 4,374,888 A | 2/1983 | Bornslaeger | |
| 4,560,385 A | 12/1985 | Baravian | 8/115.7 |
| 4,690,679 A | 9/1987 | Mattingly, III et al. | |
| 4,713,069 A | 12/1987 | Wang et al. | 604/378 |
| 4,758,239 A | 7/1988 | Yeo et al. | 604/366 |
| 4,777,073 A | 10/1988 | Sheth | 428/155 |
| 4,818,464 A | 4/1989 | Lau | 264/510 |
| 4,818,600 A | 4/1989 | Braun et al. | 428/290 |
| 4,904,249 A | 2/1990 | Miller et al. | 604/378 |
| 5,145,727 A | 9/1992 | Potts et al. | 428/198 |
| 5,169,706 A | 12/1992 | Collier, IV et al. | 428/152 |
| 5,176,668 A | 1/1993 | Bernardin | 604/378 |
| 5,178,931 A | 1/1993 | Perkins et al. | 428/198 |
| 5,188,885 A | 2/1993 | Timmons et al. | 428/198 |
| 5,236,427 A | 8/1993 | Hamajima et al. | 604/378 |
| 5,263,948 A | 11/1993 | Karami et al. | 604/383 |
| 5,336,552 A | 8/1994 | Strack et al. | 428/224 |
| 5,346,487 A | 9/1994 | Lovestedt | |
| 5,382,400 A | 1/1995 | Pike et al. | 264/168 |
| 5,387,208 A | 2/1995 | Ashton et al. | 604/378 |
| 5,409,761 A | 4/1995 | Langley | 428/198 |
| 5,415,716 A | 5/1995 | Kendall | 156/256 |
| 5,458,592 A | 10/1995 | Abuto et al. | 604/378 |
| 5,516,572 A | 5/1996 | Roe | 428/131 |
| 5,527,303 A | 6/1996 | Milby, Jr. et al. | |
| 5,558,658 A | 9/1996 | Menard et al. | |
| 5,571,096 A | 11/1996 | Dobrin et al. | 604/383 |
| 5,643,239 A | 7/1997 | Bodford et al. | 604/370 |
| 5,649,916 A | 7/1997 | DiPalma et al. | 604/378 |
| 5,674,214 A | 10/1997 | Visscher et al. | |
| 5,695,868 A | 12/1997 | McCormack | 428/283 |
| 5,718,699 A | 2/1998 | Brisebois | |
| 5,718,972 A | 2/1998 | Murase et al. | 428/360 |
| H1750 H | 9/1998 | Dobrin | 604/383 |
| 5,810,797 A | 9/1998 | Menard et al. | 604/378 |
| 5,817,081 A | 10/1998 | LaVon et al. | 604/378 |

FOREIGN PATENT DOCUMENTS

| | | |
|---|---|---|
| EP | 0 422 504 | 6/1995 |
| EP | 0 6740 35 | 9/1995 |
| EP | 0 852 268 | 12/1996 |
| WO | 90/00041 | 1/1990 |
| WO | 93 01780 | 2/1993 |
| WO | 95/35206 | 12/1995 |
| WO | 96/13283 | 5/1996 |
| WO | 96/19346 | 6/1996 |
| WO | 96/33680 | 10/1996 |
| WO | 97 16148 | 5/1997 |
| WO | 97/24095 | 7/1997 |
| WO | 97/24096 | 7/1997 |
| WO | 97/24097 | 7/1997 |
| WO | 97/36562 | 10/1997 |
| WO | 98/03138 | 1/1998 |
| WO | 98/29480 | 7/1998 |
| WO | 98/33464 | 8/1998 |
| WO | 98/38957 | 9/1998 |

ABSORBENT ARTICLES HAVING REDUCED OUTER COVER DAMPNESS

TECHNICAL FIELD

The present invention relates to absorbent articles. More particularly, the present invention relates to absorbent articles, such as personal care products, that have reduced outer cover dampness.

BACKGROUND OF THE INVENTION

Absorbent articles, such as infant diapers, adult incontinence garments, sanitary napkins, bedpads, panty liners, incontinent pads, and the like are well known in the art. These articles are inexpensive, often disposable, and yet capable of absorbing and retaining fluids and other bodily discharges. These absorbent articles typically have an outer cover having a liquid-impermeable plastic film, such as polypropylene and/or polyethylene, to prevent the retained discharge from leaking from the article and soiling items of clothing, bedding, furniture, and the like. However, until recently liquid-impermeable outer covers often employed a film which was impervious to water vapor as well as liquids. Because the outer cover was impermeable to both liquids and water vapor, the absorbent article often felt hot and clammy to the wearer even prior to absorbing any bodily discharge. Furthermore, this lack of permeability to water vapor often caused irritation of the skin and in some cases severe dermatological problems. For example, absorbent articles such as diapers may cause diaper rash on infants when worn for considerable periods of time. In addition to concerns over skin wellness, the liquid impermeable plastic films employed as outer covers often lacked the aesthetic and tactile qualities desired in personal care products such as disposable diapers.

In response to the problems described above, breathable cloth-like liquid-impermeable outer covers have been developed. Such structures, typically laminates of several different sheets, remain substantially impervious to liquids but are "breathable" in the sense that water vapor will pass through the outer cover. Breathable outer covers have become increasingly popular and more highly commercialized in absorbent personal care products, particularly in connection with disposable diapers. However, while providing a healthier and more comfortable product from the wearer's perspective, breathable liquid-impervious outer covers often suffer from an unwanted and unpleasant outer cover dampness. Continued use of an absorbent article after fluid has been discharged and absorbed by the article can, even after a short time, cause the outer cover to develop a wet or damp feel. However, this unpleasant wet feeling is not typically due to permeation of liquid through the liquid-impermeable cover or leakage from the article but is simply condensation of water vapor on the outer cover as a result of excess water vapor passing through the outer cover.

Thus, there exists a need for an absorbent article which allows sufficient water vapor permeation for absorbent articles to remain a healthy and comfortable product for the wearer but which does not allow excessive water vapor permeation after discharge of fluid into the article such that the outer cover develops a wet or damp feel.

SUMMARY OF THE INVENTION

The present invention addresses the difficulties and problems discussed above as well as problems experienced by those skilled in the art by providing an absorbent article comprising: (a) a breathable liquid-impervious outer cover; (b) a liquid pervious topsheet; (c) an absorbent body between the outer cover and topsheet; and (d) a hydrophobic barrier layer positioned between the breathable outer cover and the absorbent body. The hydrophobic barrier layer can comprise one or more layers of porous material having a supported hydrohead value at least 18 cm and a bulk of at least about 0.012 inches (0.03 cm) and further wherein the outer cover and barrier layer collectively have an inverted-WVTR of less than about 15,000 $g/m^2$/day. Desirably the porous material has a hydrohead of at least 30 mbar and, still further, comprises a fibrous material such as a woven fabric or nonwoven web. In a further aspect, hydrophobic barrier layer can comprise a nonwoven web having a Frazier air permeability over 20 cubic feet per square foot per minute. The barrier layer may comprise, in one aspect, one or more nonwoven webs of meltblown fibers having a collective basis weight of over 16 $g/m^2$ (grams per square meter). In still a further aspect, the barrier layer can comprise a plurality of layers, including a layer of meltblown fibers, wherein the plurality of layers have a collective basis weight in excess of about 20 $g/m^2$, desirably having a basis weight from about 25 $g/m^2$ to about 40 $g/m^2$. In a further aspect, the hydrophobic barrier layer may comprise at least one spunbond layer and one meltblown layer.

In a further aspect, the absorbent article includes a hydrophobic barrier layer that extends under substantially the entire portion of the absorbent body. For example, the hydrophobic barrier layer can extend beyond outer edges of the absorbent body or only along the length of the central portion of the absorbent article. In a further aspect, the barrier layer may comprise at least in part a portion of a wrapsheet about the absorbent body. For example, the wrapsheet can comprise a hydrophobic barrier layer over a first side of the absorbent body adjacent the outer cover and a hydrophilic nonwoven layer over the opposed side of the absorbent body adjacent the topsheet. Alternatively, the wrapsheet can comprise a continuous sheet having a hydrophobic portion adjacent the liquid-impervious outer cover and a hydrophilic portion over the opposed side of said absorbent body and adjacent the topsheet such that the hydrophobic portion of the wrapsheet comprises at least part of the hydrophobic barrier layer.

DEFINITIONS

Figure 1:
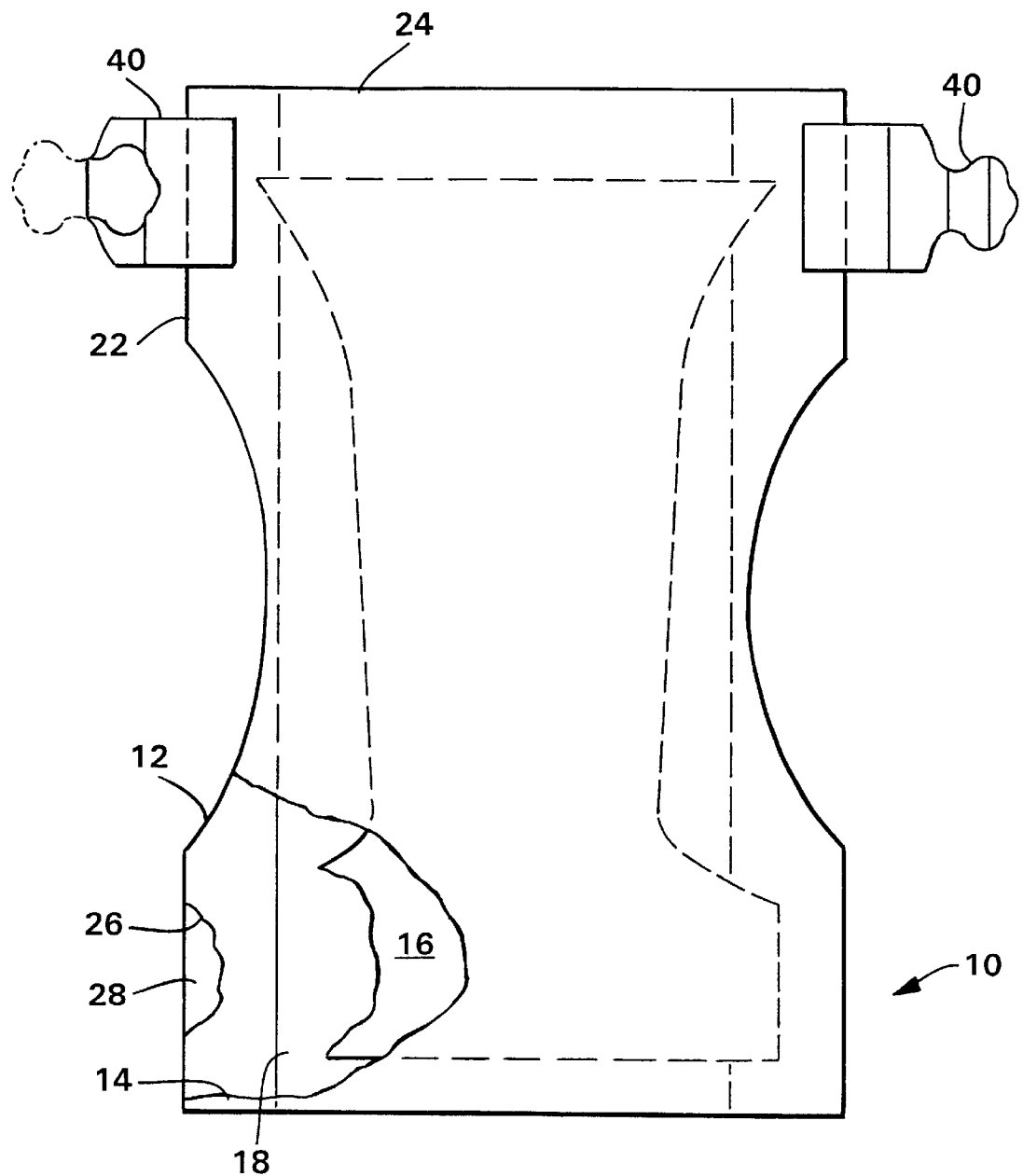
FIG. 1 is a representative partially cut away plan view of a diaper of the present invention in a flat, uncontracted state.

As used herein the term "nonwoven fabric" or "nonwoven web" means a web having a structure of individual fibers or threads which are interlaid, but not in an identifiable manner as in a knitted fabric. Nonwoven fabrics or webs have been formed from many processes such as for example, meltblowing processes, spunbonding processes, hydroentangling, and bonded carded web processes.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced such as, for example, described in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338, 992 and 3,341,394 to Kinney, U.S. Pat. No. 3,502,763 to Hartman, U.S. Pat. No. 3,542,615 to Dobo et al., U.S. Pat. No. 5,336,552 to Strack et al. and U.S. Pat. No. 5,382,400 to Pike et al. Spunbond fibers are generally not tacky when they are deposited onto a collecting surface. Thus, webs of spunbond fibers are commonly treated to impart additional integrity to the web such as, for example, described in commonly assigned U.S. patent application Ser. No. 08/362, 328 to Arnold et al. filed Dec. 22, 1994, U.S. Pat. No. 4,374,888 to Bornslaeger, and U.S. Pat. No. 3,855,046 to Hansen and Pennings. Spunbond fibers are generally continuous and often have average diameters (from a sample of at least 10) larger than 7 microns, more particularly, between about 10 and 50 microns. However, fine fiber spunbond materials may be produced and, as used herein, include fibers having a denier of 2 or below.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed in various patents and publications, for example, in U.S. Pat. No. 3,849,241 to Butin et al.; NRL Report 4364, "Manufacture of Super-Fine Organic Fibers" by V. A. Wendt, E. L. Boone and C. O. Fluharty; NRL Report 5265, "An Improved Apparatus for the Formation of Super-Fine Thermoplastic Fibers" by K. D. Lawrence, R. T. Lukas, and J. A. Young. Meltblown fibers are generally microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometric configurations of the molecules. These configurations include, but are not limited to, isotactic, syndiotactic and random symmetries.

As used herein "multilayer laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 4,374,888 to Bornslaeger, U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described in the aforesaid references. Alternatively, the fabric layers may be made individually, collected in rolls, and combined in a separate bonding step. Multilayer laminates may also have various numbers of meltblown layers or multiple spunbond layers in many different configurations and may include other materials such as films (F) or coform materials, e.g. SMMS, SFS, etc.

As used herein, the term "coform" means a process in which at least one meltblown diehead is arranged near a chute through which other materials are added to the web while it is forming. Such other materials may be pulp, superabsorbent particles, cellulose or staple fibers, for example. Coform processes are described in commonly assigned U.S. Pat. Nos. 4,818,464 to Lau and 4,100,324 to Anderson et al.

As used herein "point bonding" means bonding one or more layers of fabric at a plurality of discrete bond points. For example, thermal point bonding generally involves passing one or more layers to be bonded between heated rolls such as, for example an engraved pattern roll and a smooth calender roll. The engraved roll is patterned in some way so that the entire fabric is not bonded over its entire surface, and the anvil roll is usually flat. As a result, various patterns for engraved rolls have been developed for functional as well as aesthetic reasons. One example of a pattern has points and is the Hansen Pennings or "H&P" pattern with about a 30% bond area when new and with about 200 bonds/square inch as taught in U.S. Pat. No. 3,855,046 to Hansen and Pennings. Another typical point bonding pattern has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15% when new. Yet another common pattern is the C-Star pattern which has, when new, a bond area of about 16.9%. The C-Star pattern has a cross-directional bar or "corduroy" design interrupted by shooting stars. Other common patterns include a diamond pattern with repeating and slightly offset diamonds with about a 16% bond area. Typically, the percent bonding area is less than about 50% and more desirably varies from around 10% to around 30% of the area of the fabric laminate web.

As used herein a "superabsorbent" or "superabsorbent material" refers to a water-swellable, water-soluble organic or inorganic material capable, under favorable conditions, of absorbing at least about 20times its weight and, more desirably, at least about 30 times its weight in an aqueous solution containing 0.9 weight percent sodium chloride. Organic materials suitable for use as a superabsorbent material in conjunction with the present invention include, but are not limited to, natural materials such as guar gum, agar, pectin and the like; as well as synthetic materials, such as synthetic hydrogel polymers. Such hydrogel polymers include, for example, alkali metal salts of polyacrylic acids, polyacrylamides, polyvinyl alcohol, ethylene, maleic anhydride copolymers, polyvinyl ethers, methyl cellulose, carboxymethyl cellulose, hydroxypropylcellulose, polyvinylmorpholinone, and polymers and copolymers of vinyl sulfonic acid, polyacrylates, polyacrylamides, polyvinylpyrridine, and the like. Other suitable polymers include hydrolyzed acrylonitrile grafted starch, acrylic acid grafted starch, and isobutylene maleic anhydride polymers and mixtures thereof. The hydrogel polymers are preferably lightly crosslinked to render the materials substantially water insoluble. Crosslinking may, for example, be accomplished by irradiation or by covalent, ionic, van der Waals, or hydrogen bonding. The superabsorbent materials may be in any form suitable for use in absorbent composites including particles, fibers, flakes, spheres and the like. Typically the superabsorbent material is present within the absorbent body in an amount from about 5 to about 95 weight percent based on total weight of the absorbent body. Superabsorbents are generally available in particle sizes ranging from about 20 to about 1000 microns. An example of a suitable commercially available superabsorbent is SANWET IM 3900 available from Hoescht Celanese located in Portsmouth, Va. and DRYTECH 2035LD available from Dow Chemical Co. located in Midland, Mich.

As used herein, the term "breathable" means a material which is permeable to water vapor as measured by the water vapor transmission test discussed herein below, having a WVTR of at least 1500 g/m$^2$/24 hours.

As used herein, the term "personal care product" means diapers, training pants, absorbent underpants, adult incontinence products, feminine hygiene products and the like.

DESCRIPTION OF THE INVENTION

Absorbent articles generally include a liquid permeable topsheet, which faces the wearer, and a liquid-impermeable bottom sheet or outer cover. Disposed between the topsheet and outer cover is an absorbent core, often the topsheet and outer cover are sealed to encase the absorbent core. Although the following detailed description will be made in the context of a disposable diaper, one skilled in the art will appreciate that the concepts of the present invention would also be suitable for use in connection with other types of absorbent articles, particularly other personal care products. In addition, although the present invention is described in the context of several specific configurations, it will be appreciated that further combinations or alterations of the specific configurations discussed below may be made by one skilled in the art without departing from the spirit and scope of the present invention.

A diaper 10, as shown in FIG. 1, may comprise a liquid-impervious breathable outer cover 12, a liquid permeable topsheet 14 positioned in facing relation to the outer cover 12, and an absorbent core 16 between the outer cover 12 and topsheet 14. Disposed between the absorbent core 16 and the breathable outer cover 12 is a hydrophobic breathable barrier layer 18.

The diaper 10 may be of various shapes such as, for example, an overall rectangular shape, T-shape or an hour glass shape. The topsheet 14 is generally coextensive with the outer cover 12 but may optionally cover an area which is larger or smaller than the area of the outer cover 12, as desired. Portions of the diaper 10, such as a marginal section of the outer cover 12, may extend past the terminal edges of the absorbent core 16. In the illustrated embodiment, for example, the outer cover 12 can extend outwardly beyond the terminal marginal edges of the absorbent core 16 to form side margins 22 and end margins 24 of the diaper 10.

The topsheet 14, as representatively illustrated in FIG. 1, preferably presents a body facing surface which is compliant, soft to the touch, and non-irritating to the wearer's skin. The topsheet 14 is suitably employed to help isolate the wearer's skin from liquids held in the absorbent core 16. In order to present a dryer surface to the wearer, the topsheet 14 may be less hydrophilic than the absorbent core 16 and also sufficiently porous to be readily liquid permeable. Topsheets are well known in the art and may be manufactured from a wide variety of materials, such as porous foams, reticulated foams, apertured plastic films, natural fibers (i.e., wool or cotton fibers), synthetic fibers (i.e., polyester, polypropylene, polyethylene, etc.), or a combination of natural and synthetic fibers. For example, the topsheet may comprise meltblown or spunbonded web of polyolefin fibers or a bonded-carded web composed of natural and/or synthetic fibers. In this regard the topsheet may be composed of substantially hydrophobic material treated with a surfactant or otherwise processed to impart the desired level of wettability and permeability. As an example, surfactant may be applied, in an amount to impart the desired degree of hydrophilicity, by conventional means, such as spraying, printing, brush coating or the like. In a preferred embodiment, the topsheet may comprise a nonwoven web of polypropylene spunbond fibers or polyethylene/propylene multicomponent spunbond fibers treated with a surfactant, octylphenoxypolyethoxyethanol, commercially available from Union Carbide of Danbury, Conn. under the trademark TRITON X-102.

The backsheet or outer cover 12 may comprise a breathable liquid-impervious structure and may often comprise a multilayer laminate. In the particular embodiment shown in FIG. 1, the outer cover comprises a breathable liquid impervious film 26 and one or more additional nonwoven layers 28 (shown in FIG. 1 as a single layer). The particular structure and composition of the outer cover may be selected from various combinations of films and/or nonwovens; the nonwovens layers are generally selected for providing the desired strength, abrasion resistance, tactile properties and/or aesthetics. In particular, it is preferred that the outer most portion of the outer cover 12, such as nonwoven layer 28 as shown in FIG. 1, comprise a durable material having a cloth-like feel and good abrasion resistance, such as an SMS laminate. Liquid-impervious outer covers comprising multilayer laminates having thin non-porous films, such as polyvinyl alcohol, which allow the migration of water vapor through the film itself are known in the art. In addition, films which are rendered breathable, but which remain liquid-impervious, by the formation of microporous voids sized to allow the transmission of water vapor therethrough are likewise known in the art. Multilayer laminates incorporating the latter type of breathable films are generally preferred. These films may be rendered vapor permeable by adding filler particles to the film composition and either rolling or stretching the film causing fractures to form where the filler particles are located. The amount of filler within the film and the degree of stretching and/or rolling is controlled to impart the desired degree of vapor permeability. These films are typically formed from a polyolefin film, such as polyethylene or polypropylene. Examples of breathable liquid-impervious films and liquid-impervious multilayer laminates are disclosed in U.S. Pat. No. 4,777,073 issued to Sheth, U.S. Pat. No. 4,818,600 issued to Braun et al., and World Publication No. WO95/16562 and World Publication No. WO96/19346 and commonly assigned U.S. patent application Ser. No. 08/929,562 filed Sep. 15, 1997 to McCormack et al., the entire contents of the aforesaid references are incorporated herein by reference. A particularly desirable material for use in liquid impervious breathable multilayer laminates is a biaxially oriented polyethylene microporous film material which is about 50 weight percent calcium carbonate and which is commercially available from Exxon Chemical Co., Inc. of Linden, N.J. under the trade name EXXAIRE.

Between the breathable liquid-impervious outer cover 12 and the liquid pervious topsheet 14 is positioned an absorbent core 16 which typically includes superabsorbent particles and, optionally, additional absorbent materials such as absorbent fibers including, but not limited to, wood pulp fluff fibers, synthetic wood pulp fibers, synthetic fibers and combinations thereof. A common problem with wood pulp fluff, however, is its lack of integrity and a tendency to collapse when wet. Thus, it is often advantageous to add a stiffer reinforcing fiber such as polyolefin meltblown fibers or shorter length staple fibers, typically provided as a coform material. For example, as indicated above, superabsorbent particles and/or staple fibers such as wood pulp may be injected into meltblown fiber stream so as to be entrapped or bonded to the meltblown fibers. The superabsorbent materials may be substantially homogeneously mixed with the hydrophilic fibers or may be selectively placed into desired zones of the absorbent body to better contain and absorb body exudates. The concentration of the superabsorbent materials may also vary through the thickness of the absorbent core. Alternatively, the absorbent core may comprise a laminate of fibrous webs and superabsorbent materials or other suitable means for maintaining superabsorbent in localized areas.

The absorbent core may have any of a number of shapes. For example, the absorbent core may be rectangular, I-shaped, or T-shaped. It is generally preferred that the absorbent core be narrower in the crotch area than in the front or rear portions of the diaper. The size of the absorbent core and selection of materials therein will vary with the desired loading capacity, the intended use of the absorbent article and other factors known to those skilled in the art.

The absorbent core 16 may, optionally, have a hydrophilic tissue wrapsheet (not shown in FIG. 1). The tissue wrapsheet helps to maintain the integrity of some absorbent structures, such as airlaid fibrous structures. In addition, the tissue wrapsheet also helps to distribute liquid over the mass of the absorbent body, particularly when using a material with excellent wicking properties such as absorbent cellulosic materials. Examples of common tissue wrapsheet materials include creped wadding or a high wet-strength tissue. In addition, hydrophilic nonwoven fabrics may also be used as an absorbent core wrapsheet; see commonly assigned U.S. Pat. No. 5,458,592 to Abuto et al., the entire contents of which are incorporated herein by reference.

Separating the absorbent core 16 and the breathable outer cover 12 is a breathable hydrophobic barrier layer 18. In this regard it has, surprisingly, been found that certain materials will not appreciably limit the WVTR of the diaper in the dry state yet significantly decrease the WVTR of the diaper once the absorbent core has absorbed fluids. Thus, the hydrophobic barrier layer of the present invention will allow sufficient water vapor transmission, when the absorbent article is in a dry state, such that the WVTR of the diaper is not appreciably lowered and the diaper remains breathable. However, when the absorbent core has absorbed liquid discharged from the body the hydrophobic barrier will act to substantially lower the WVTR of the absorbent article (relative to the same article without a hydrophobic barrier layer), thereby reducing or eliminating the wet or clammy feeling which may develop on the outer portion of the backsheet due to condensation.

The breathable liquid-impervious outer cover 12 and hydrophobic barrier layer 18 collectively have an inverted-WVTR, as described herein below, of less than 15,000 g/m$^2$/day, desirably less than about 12,000 g/m$^2$/day and still more desirable less than about 11,000 g/m$^2$ day. However, the outer cover 12 and hydrophobic barrier layer 18 have a WVTR over 1500 g/m$^2$/day, desirably over 4000 g/m$^2$/day. Although the hydrophobic barrier layer 18 does not need to have liquid-barrier properties to the same degree as the liquid-impervious outer covers described above, it does need to have certain "barrier" like properties in order to selectively control the WVTR and limit outer cover dampness. In this regard, suitable materials are those which are hydrophobic with a hydrohead value of at least 18 cm, preferably from about 30 cm to about 50 cm. In addition, the hydrophobic barrier should have a thickness or bulk of at least about 0.012 in. (0.03 cm), preferably between about 0.018 in. (0.046 cm) to about 0.048 in. (0.122 cm). The hydrophobic barrier layer desirably also has a Frazier air permeability of at least 20 cubic feet per square foot per minute (about 6095 liters/square meter/minute) and more desirably over about 40 ft.$^3$/ft.$^2$/min. (about 12192 liters/m$^2$/min.).

The hydrophobic barrier layer may comprise breathable fibrous materials such as a woven or nonwoven fabric having the above properties, including but not limited to, meltblown webs, fine fiber spunbond webs such as those having fiber deniers of about 2 or less, bonded and carded webs, hydroentangled fabrics and other fabrics having the similar properties. Suitable polymeric materials for making the barrier layer include those capable of making fibrous webs; examples include but are not limited to polyamides, polyesters and polyolefins, such as polyethylene and/or polypropylenes. In a preferred aspect the hydrophobic barrier layer may comprise a meltblown web of polypropylene fibers having a basis weight from 16 to about 64 g/m$^2$, more desirably in excess of about 20 g/m$^2$ up to about 40 g/m$^2$. The fibrous barrier layer 18 may comprise a single sheet or multiple layered sheets which collectively have the desired characteristics. However, when using multiple layered sheets, it is desirable that they be juxtaposed without being point bonded across a substantial surface area of the layers or otherwise bonded in a manner which would substantially limit the breathability of the layers. Similarly, in a preferred embodiment the hydrophobic barrier layer is not thermally point bonded or otherwise laminated to the liquid-impervious outer cover in a manner which destroys the breathability of the article. In this regard, it may be desirable that the breathable hydrophobic barrier layer be attached to the absorbent article primarily at the periphery of the hydrophobic barrier layer. The multiple layers can be bonded thermally, ultrasonically, adhesively or by other means known in the art.

In one aspect, as shown in FIG. 1, the hydrophobic barrier sheet 18 may be positioned between the absorbent core 16, which optionally includes a hydrophilic wrapsheet (not shown), and outer cover 12. The barrier sheet should extend under at least those regions of the absorbent core 16 which typically retain the majority of the bodily discharge. The hydrophobic barrier sheet 18 preferably also extends under substantially the entire portion of the absorbent core 16 and may also further extend beyond the edges of the same. As shown in FIG. 1, the hydrophobic barrier sheet 18 may extend along the length of the central portion of the diaper 10 underneath the absorbent core 16. Diaper configurations in which the barrier extends under the entirety of the absorbent core are highly preferred where the absorbent core 16 includes a hydrophilic wrapsheet with good wicking characteristics, such as when using a tissue core wrap.

Figure 4:
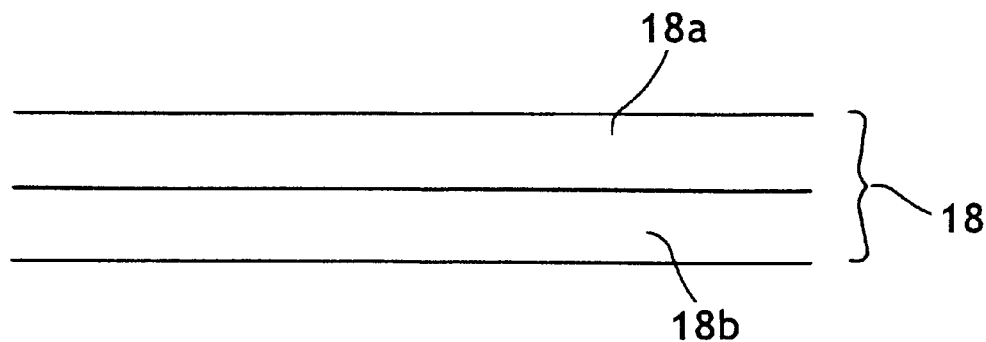
FIG. 4 and FIG. 5 depict a cross-sectional view of the hydrophobic barrier sheet.
Figure 5:
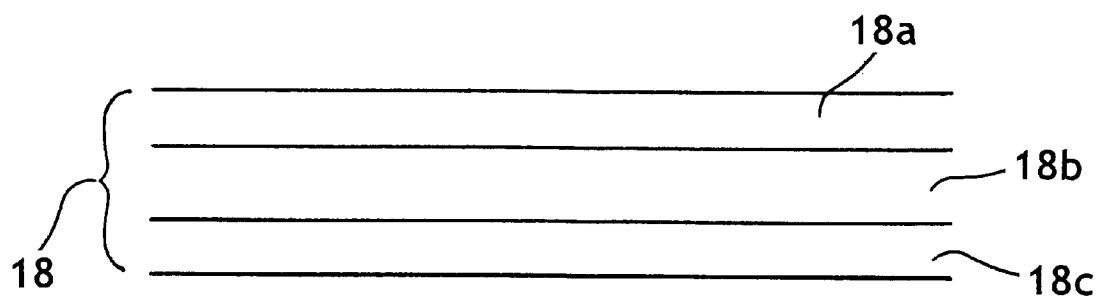

In a further aspect, and in reference to FIG. 4, hydrophobic barrier sheet 18 can comprise one or more layers such as, for example, a first layer 18a and second layer 18b. The multiple layers can comprise combinations of materials described herein and including, but not limited to, meltblown/spunbond and spunbond/film. Still further, and in reference to FIG. 5, hydrophobic barrier sheet 18 can itself comprise three layers 18a, 18b, 18c respectively. The multiple layers can include combinations of materials described herein and including, but not limited to, spunbond/meltblown/spunbond, spunbond/film/spunbond, and meltblown/spunbond/meltblown.

In a further aspect of the invention, the barrier layer may comprise at least a portion of the absorbent core wrapsheet. The barrier layer may be sufficiently wide so that it may be folded over on itself and then sealed using, for example, adhesives, heat, ultrasonic and/or pressure on either the top, bottom or sides of the wrapsheet. Folding of the barrier layer may be accomplished through the use of conventional sheet folding means such as curved plates which work the barrier sheet over onto itself. However, when a continuous sheet of barrier fabric is used to encapsulate the absorbent core 16, such as wrapsheet 30, selected portions of the sheet are preferably treated so that those areas adjacent the liquid pervious topsheet 14 are hydrophilic. This may be accomplished by zone treating the barrier layer with a surfactant to impart wettability to specific areas.

Figure 2:
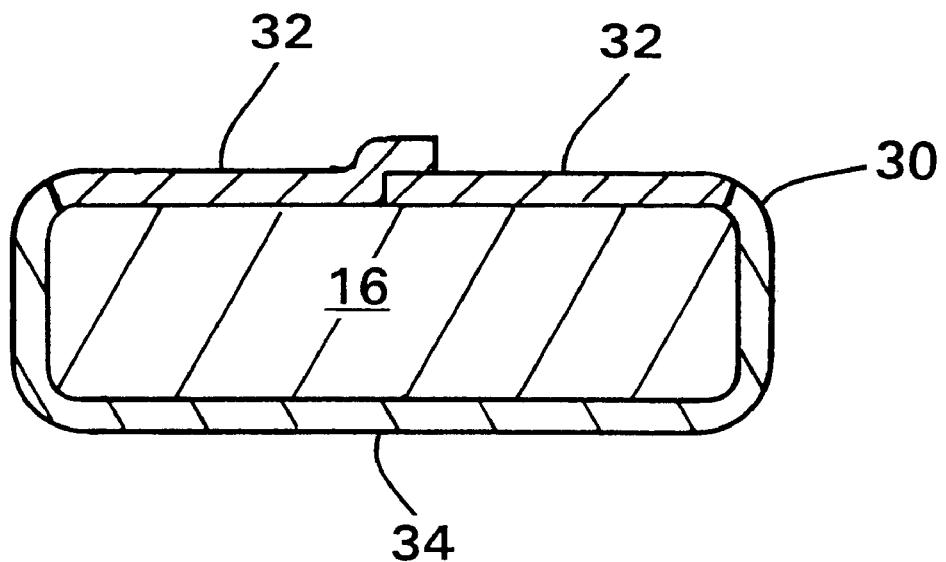
FIG. 2 is a cross-sectional side view of an absorbent core and wrapsheet.

Thus, as shown in FIG. 2, the absorbent core wrapsheet 30 may comprise a continuous sheet having hydrophilic regions 32 over a first side of the absorbent core 16 and hydrophobic regions 34 over the opposite side of the absorbent core 16. When integrated into the diaper as shown in FIG. 1, the hydrophilic regions would be facing the liquid pervious topsheet 14 and the opposed hydrophobic region would comprise at least a portion of the barrier layer.

Figure 3:
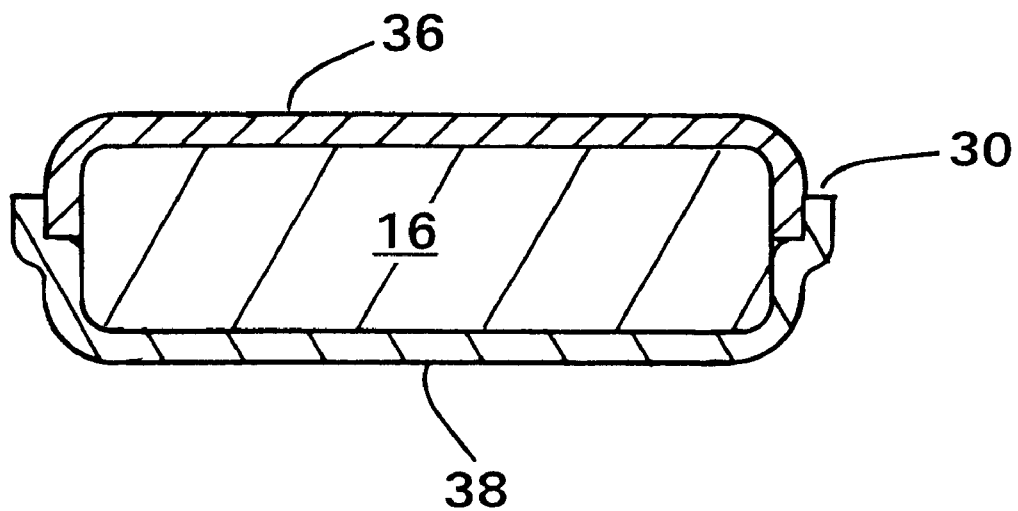
FIG. 3 is a cross-sectional side view of an absorbent core and wrapsheet.

In an alternate embodiment the absorbent core may have a wrapsheet 30 comprising two or more sheets joined together. For example, as shown in FIG. 3, the wrapsheet 30 may comprise a hydrophilic liquid permeable sheet 36 on the side of the absorbent core 12 adjacent the wearer's side, that is adjacent topsheet 14 of FIG. 1, and a hydrophobic barrier sheet 38 adjacent the opposed side of the absorbent core 16. The two sheets 36 and 38 collectively form wrapsheet 30 and may be sealed by one of various means in the art such by the use of adhesive, thermal, ultrasonic and/or pressure bonding.

In addition, the diaper 10, as represented in FIG. 1, may further include a pair of fasteners 40 which are employed to secure the diaper 10 about the waist of the wearer (not shown). Suitable fasteners include hook-and-loop type fasteners, adhesive tape fasteners, buttons, snaps, mushroom-and-loop fasteners and the like. Furthermore, although not discussed above, one skilled in the art will recognize that additional components may be integrally incorporated within the diaper without departing from the spirit of the present invention. For example, it is common for diapers to include elasticized leg bands (not shown) which help secure the diaper to the wearer and, thus, help reduce leakage from the diaper. Similarly, it is also known to include a pair of elasticized, longitudinally extending containment flaps (not shown) which are configured to maintain a substantially upright, perpendicular arrangement along the central portion of the diaper to serve as an additional barrier to the lateral flow of body exudates. Further, it is also common to include a surge management layer positioned between the topsheet 14 and the absorbent core 16 in order to help prevent pooling of fluids on the portion of the diaper adjacent the wearer's skin. These and other components are well known and the manner and method of using the same in connection with the absorbent article of the present invention will likewise be readily appreciated by those skilled in the art.

The various components of the diaper are integrally assembled together employing various means of attachment known to those skilled in the art such as, for example, adhesive bonding, ultrasonic bonds, thermal bonds or combinations thereof.

Test Procedures

Bulk: A measure of the thickness of a fabric. The bulk or thickness may be determined in accord with ASTM Standard Test Method for Thickness of Nonwoven Fabrics D 5729-95 using a three inch acrylic platen which provides 0.05 psi loading.

Hydrohead: A measure of the liquid barrier properties of a fabric is the hydrohead test. The hydrohead test determines the height of water or amount of water pressure (in millibars) that the fabric will support before liquid passes therethrough. A fabric with a higher hydrohead reading indicates it has a greater barrier to liquid penetration than a fabric with a lower hydrohead. The hydrohead can be performed according to Federal Test Standard 191A, Method 5514. The hydrohead data cited herein was obtained using a test similar to the aforesaid Federal Test Standard except modified as noted below. The hydrohead was determined using a hydrostatic head tester available from Marlo Enterprises, Inc. of Concord, N.C. The specimen is subjected to a standardized water pressure, increased at a constant rate until the first sign of leakage appears on the surface of the fabric in three separate areas. (Leakage at the edge, adjacent clamps is ignored.) Unsupported fabrics, such as a thin film, can be supported to prevent premature rupture of the specimen.

Frazier Permeability: A measure of the permeability of a fabric or web to air is the Frazier Permeability which is performed according to Federal Test Standard 191A, Method 5450 dated Jul. 20, 1978, and is reported as an average of 3 sample readings. Frazier Permeability measures the air flow rate through a web in cubic feet of air per square foot of web per minute or CFM. Conversion of CFM to liters per square meter per minute (LMM) may be accomplished by multiplying CFM by 304.8.

WVTR: The water vapor transmission rate (WVTR) for the sample materials was calculated in accordance with ASTM Standard E96-80. Circular samples measuring three inches in diameter were cut from each of the test materials and a control which was a piece of CELGARD2500 film from Hoechst Celanese Corporation of Sommerville, N.J. CELGARD2500 film is a microporous polypropylene film. Three samples were prepared for each material. The test dish was a number 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at 100° F. (32° C. ) or 1 hour to equilibrate. The oven was a constant temperature oven with external air circulating through it to prevent water vapor accumulation inside. A suitable forced air oven is, for example, a Blue M Power-O-Matic 60 oven distributed by Blue M. Electric Company of Blue Island, Ill. Upon completion of the equilibration, the pans were removed from the oven, weighed an immediately returned to the oven. After 24 hours, the pans were removed from the oven and weighed again. The preliminary test water vapor transmission rate values were calculated with Equation (I) below:

$$\text{Test WVTR} = (\text{grams weight loss over 24 hours}) \times 315.5 \text{ g/m}^2/24 \text{ hours} \qquad (I)$$

The relative humidity within the oven was not specifically controlled.

Under the predetermined set conditions of 100° F. (32° C.) and ambient relative humidity, the WVTR for the CELGARD2500 control has been defined to be 5000 grams per square meter for 24 hours. Accordingly, the control sample was run with each test and the preliminary test values were corrected to set conditions using Equation (II) below:

$$WVTR = (Test\ WVTR/control\ WVTR) \times (5000\ g/m^2/24\ hours) \quad (II)$$

Inverted WVTR: This test is similar to the WVTR discussed above with the exception that the cup is inverted such that the water contacts the fabric being tested. In addition, since the WVTR of CELGUARD 2500 is not 5000 g/m²/24 for the inverted test, this control and correction has been deleted from the calculations of the inverted water vapor transmission rate test. This test is believed to more accurately duplicate the vapor transfer experienced by a loaded absorbent article.

EXAMPLE 1

A propylene meltblown fiber nonwoven web was made using Himont PF-015 polypropylene polymer from Himont, USA of Wilmington, Del. The meltblown web was made in accordance with meltblowing techniques described in U.S. Pat. No. 5,458,592 using a multiple bank meltblown apparatus. The polypropylene was extruded through a multiple bank meltblown die assembly at a throughput of 2.5 pounds per inch per hour (PIH). The extruded streams of molten polymer were attenuated with primary attenuation air delivered at a rate of between about 1700 and 2000 cubic feet per minute at a temperature of 530° F. The resultant meltblown had a basis weight of 8.0 grams per square meter (g/m²) and a bulk of 0.006 inches (0.015 cm). The mean flow pore size for the sample was about 25 microns and the maximum flow pore size was 47 microns with 0.5 percent of the overall pores having a pore size greater than 50 microns. The web had a supported hydrohead of 17.6 mbar, an unsupported hydrohead of 19.5 mbar and Frazier air permeability of 287 cubic feet per square foot per minute (CFM). A sample of the meltblown web was subsequently juxtaposed with a 0.0025 cm thick film of CELGUARD 2500, without bonding or otherwise laminating the materials together. The breathable liquid-impermeable film and meltblown layer collectively had a WVTR of 5154 g/m²/day and an inverted-WVTR of 19396 g/m²/day.

EXAMPLE 2

A nonwoven web of polypropylene meltblown fibers, as described above in Example 1, was also used in the present example. Three plies of the nonwoven web were juxtaposed, without bonding or otherwise laminating the layers, an d had a collective bulk of 0.012 inches (0.03 cm), supported hydrohead of 37.7 mbar, an unsupported hydrohead of 37.4 mbar and a Frazier Air Permeability of 81.4 CFM. The 3 ply layer of nonwoven material was then juxtaposed over a breathable liquid-impervious barrier of 0.0025 cm thick film of CELGUARD 2500. The breathable film and nonwoven layer collectively had a WVTR of about 5154 g/m²/day and an inverted-WVTR of 10367 g/m²/day.

EXAMPLE 3

A nonwoven web of polypropylene meltblown fibers, as described above in Example 1, was also used in the present example. Five plies of the nonwoven were juxtaposed, without bonding or otherwise laminating the layers, and had a collective bulk of 0.017 inches (0.04 cm), supported hydrohead of 46.1 mbar, an unsupported hydrohead of 50.5 mbar and a Frazier Air Permeability of 81.4 CFM. The five ply layer of nonwoven material was subsequently juxtaposed over a breathable liquid-impervious barrier of 0.0025 cm thick film of CELGUARD 2500 without bonding or otherwise laminating the respective materials. The breathable film and nonwoven layer collectively had a WVTR of about 4528 g/m²/day and an inverted-WVTR of 12055 g/m²/day.

EXAMPLE 4

A spunbond material was made in accord with the teachings described herein above resulting in a 0.5 osy (17 g/m²) web of continuous spunbond fibers. The spunbond layer was juxtaposed with two layers of meltblown webs of Example 1 such that the spunbond layer was positioned between the two meltblown layers. The meltblown/spunbond/meltblown material was not bonded or otherwise laminated together. The 3 ply layer had a bulk of 0.016 inches (0.04 cm), supported hydrohead of 38.0 mbar, an unsupported hydrohead of 39.7 mbar and Frazier Air Permeability of 112.4 CFM. The 3 ply layer of nonwoven material was then juxtaposed over a breathable liquid-impervious barrier of 0.0025 cm thick film of CELGUARD 2500 without bonding or otherwise laminating the respective-materials. The breathable liquid-impervious film and nonwoven layers collectively had a WVTR of about 4609 g/m²/day and an inverted-WVTR of 10739 g/m²/day.

EXAMPLE 5

A meltblown web made in of Example 1 was juxtaposed with two spunbond webs of Example 4 such that the meltblown web was positioned between the two spunbond layers. The 3 ply layer had a bulk of 0.019 inches (0.05 cm) supported hydrohead of 27.4 mbar, an unsupported hydrohead of 29.3 mbar and Frazier Air Permeability of 181 CFM. The 3 ply layer was subsequently juxtaposed with an 0.0025 cm thick film of CELGUARD 2500 without bonding or laminating the respective materials. The breathable liquid-impermeable film and 3 ply layer collectively had a WVTR of 4415 g/m²/day and an inverted-WVTR of 11,486 g/m²/day.

EXAMPLE 6

A 0.0025 cm thick film of CELGUARD 2500 was juxtaposed with two layers of spunbond fibers of Example 4 such that the breathable film was between the two spunbond layers. The 3-ply layer had a bulk of 0.018 inches (0.046 cm), supported hydrohead of 206.8 mbar, an unsupported hydrohead of 190.9 mbar and Frazier Air Permeability of 0.172 CFM. The 3 ply layer was subsequently juxtaposed with an 0.0025 cm thick film of 0.0025 cm thick film of CELGUARD 2500 without bonding or otherwise laminating the respective materials together. The breathable film and 3 ply layer collectively had a WVTR of 4652 g/m²/day and an inverted-WVTR of 12,315 g/m²/day.

As may be appreciated by the foregoing examples, it has been surprisingly found that certain materials have little effect on the WVTR of an absorbent article when dry yet significantly reduce the WVTR of the absorbent article when loaded. In reference to Example 1, the 0.006 thick meltblown material, in conjunction with the CELGUARD 2500, had an excellent WVTR of 5153 CFM and a correspondingly high inverted-WVTR of 19396 CFM. However, the multiply meltblown layer having a bulk of about 0.012 inches (0.03 cm) also had a good WVTR of 4807 CFM. However, the inverted-WVTR of Example 2 was but 10376 CFM. Thus, the bulkier meltblown, while not appreciably limiting the WVTR, dramatically reduced the inverted-WVTR relative to both the control and Example 1 by about 50%. Accordingly, an absorbent article employing such a barrier layer would have the desired breathability when dry yet would have a reduced WVTR when the article is loaded, thereby reducing or eliminating outer over dampness caused by condensation. Comparable results are obtained by other material layers with the requisite functional characteristic described herein above. Further, as shown in Example 6, these results are comparable to those employing a second breathable liquid-impervious layer. However, one skilled in the art will appreciate that the high costs associated with breathable liquid-impervious covers, such as microporous films, may be avoided with the absorbent articles of the present invention.

While the invention has been particularly shown and described with reference to preferred embodiments thereof, it will be understood by those skilled in the art that other changes in form and details may be made therein without departing from the spirit and scope of the invention.

What is claimed is:

1. An absorbent article comprising:
   an outer cover comprising a liquid impervious film and wherein the outer cover has a WVTR over 1500 g/m²/ 24 hours;
   a liquid pervious topsheet;
   an absorbent body situated between said outer cover and said topsheet; and
   a hydrophobic porous barrier layer having a WVTR over 1500 g/m²/24 hours, a hydrohead value of at least 18 cm and a bulk of at least about 0.03 cm and situated between said outer cover and said absorbent body, said porous barrier layer comprising a hydrophobic fibrous material selected from the group consisting of non-woven webs and woven fabrics and further wherein said outer cover and porous barrier layer collectively have an inverted-WVTR of less than about 15,000 g/m²/day.

2. The absorbent article of claim 1 wherein said fibrous material comprises polyolefin fibers.

3. The absorbent article of claim 2 wherein said outer cover comprises a multilayer laminate and wherein said multilayer laminate comprises said liquid impervious film and at least one nonwoven web.

4. The absorbent article of claim 3 wherein said fibrous material comprises at least one meltblown fiber nonwoven web.

5. The absorbent article of claim 4 wherein said porous barrier layer has a basis weight between 16 g/m² and about 64 g/m².

6. The absorbent article of claim 5 wherein the liquid impervious film comprises a microporous film.

7. The absorbent article of claim 3 wherein said fibrous material comprises a meltblown fiber nonwoven web and a spunbond fiber nonwoven web.

8. The absorbent article of claim 7 wherein said porous barrier layer has a basis weight between 16 g/m² and about 64 g/m².

9. The absorbent article of claim 8 wherein the liquid impervious film comprises a microporous film and further wherein said porous barrier layer has a hydrohead value of at least 30 cm.

10. The absorbent article of claim 9 wherein said meltblown layer is adjacent said absorbent core.

11. The absorbent article of claim 3 wherein said fibrous material comprises first and second spunbond fiber nonwoven webs and at least one meltblown fiber nonwoven web situated between said first and second spunbond fiber nonwoven webs.

12. The absorbent article of claim 3 wherein said porous barrier layer extends under substantially the entire portion of said absorbent body.

13. The absorbent article of claim 12 wherein the absorbent article has as its longest dimension a length when in a flat, uncontracted state and further wherein the porous barrier layer is centrally located within the absorbent article and extends lengthwise within the absorbent article.

14. The absorbent article of claim 3 wherein the porous barrier layer comprises a plurality of polyolefin fiber non-woven webs and wherein said plurality of nonwoven webs have a hydrohead of at least about 30 mbar and a basis weight in excess of about 20 g/m².

15. The absorbent article of claim 14 wherein said outer cover and said barrier layer have a WVTR over 1500 g/m²/day and an inverted-WVTR of less than 12,000 g/m²/day.

16. The absorbent article of claim 15 wherein said barrier layer has a WVTR of at least 3000 g/m²/day.

17. The absorbent article of claim 3 wherein said barrier layer has a hydrohead of at least 30 cm and comprises a layer of meltblown fibers and a layer of spunbond fibers and wherein said liquid-imperious outer cover and said barrier layer have a WVTR over 4000 g/m²/day and an inverted-WVTR of less than about 12,000 g/m²/day.

18. The absorbent article of claim 3 wherein said article comprises a personal care article.

19. The absorbent article of claim 3 wherein said article comprises a diaper.

20. The absorbent article of claim 3 wherein said article comprises an adult incontinence garment.

21. The absorbent article of claim 1 wherein said fibrous material comprises a meltblown fiber nonwoven web and wherein said porous barrier layer has a basis weight over 16 g/m².

22. The absorbent article of claim 1 wherein said fibrous material comprises a meltblown fiber nonwoven web and a spunbond fiber nonwoven web.

23. The absorbent article of claim 22 wherein said said porous barrier layer has a basis weight in excess of about 20 g/m².

24. The absorbent article of claim 23 wherein said article comprises a personal care article.

25. The absorbent article of claim 23 wherein said article comprises a diaper.

26. The absorbent article of claim 23 wherein said article comprises an adult incontinence garment.

27. The absorbent article of claim 1 having a wrap sheet about said absorbent body wherein the absorbent body has a first side and a second side opposite said first side and further wherein said wrapsheet comprises a hydrophobic nonwoven portion extending over the first side of said absorbent body and a hydrophilic nonwoven portion extending over the second side of said absorbent body and further wherein said hydrophilic nonwoven portion is adjacent said topsheet.

28. The absorbent article of claim 1 wherein said porous barrier layer has a hydrohead value of at least about 30 cm and a basis weight in excess of about 20 g/m² and wherein said outer cover and said barrier layer have a WVTR over 3500 g/m²/day and an inverted-WVTR of less than about 12,000 g/m²/day.

* * * * *

UNITED STATES PATENT AND TRADEMARK OFFICE
CERTIFICATE OF CORRECTION

PATENT NO.     : 6,369,292 B1
DATED          : April 9, 2002
INVENTOR(S)    : Strack et al.

It is certified that error appears in the above-identified patent and that said Letters Patent is hereby corrected as shown below:

<u>Title page,</u>
Atfer item [22], insert -- Related U.S. Application Data [60]
Provisional Application No. 60/032,580, filed on December 20, 1996 --

<u>Column 1,</u>
Line 3, should read -- This application claims priority from U.S. Provisional Application No. 60/032,580 filed on December 20, 1996 --

Signed and Sealed this

Twenty-second Day of July, 2003

JAMES E. ROGAN
*Director of the United States Patent and Trademark Office*